(12) United States Patent
Zwolinski et al.

(10) Patent No.: US 8,172,772 B2
(45) Date of Patent: May 8, 2012

(54) SPECIMEN RETRIEVAL DEVICE

(75) Inventors: Andrew M. Zwolinski, Cincinnati, OH (US); James T. Spivey, Cincinnati, OH (US); Michael J. Stokes, Cincinnati, OH (US); Daniel H. Duke, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 29 days.

(21) Appl. No.: 12/332,938

(22) Filed: Dec. 11, 2008

(65) Prior Publication Data

US 2010/0152609 A1    Jun. 17, 2010

(51) Int. Cl.
*A61B 10/00* (2006.01)
*A61B 17/24* (2006.01)
*A61B 17/26* (2006.01)

(52) U.S. Cl. ........ 600/562; 600/564; 600/565; 606/110; 606/113; 606/114; 606/115

(58) Field of Classification Search .................. 600/562, 600/564, 565, 101, 104; 604/27, 35, 36; 606/113, 114, 115
See application file for complete search history.

(56) References Cited

U.S. PATENT DOCUMENTS

| | | | |
|---|---|---|---|
| 645,576 A | 3/1900 | Telsa | |
| 649,621 A | 5/1900 | Tesla | |
| 787,412 A | 4/1905 | Tesla | |
| 1,127,948 A | 2/1915 | Wappler | |
| 1,482,653 A | 2/1924 | Lilly | |
| 1,625,602 A | 4/1927 | Gould et al. | |
| 2,028,635 A | 1/1936 | Wappler | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |
| 2,504,152 A | 4/1950 | Riker et al. | |
| 2,938,382 A | 5/1960 | De Graaf | |

(Continued)

FOREIGN PATENT DOCUMENTS

AU    666310 B2    2/1996

(Continued)

OTHER PUBLICATIONS

U.S. Appl. No. 12/133,109, filed Jun. 4, 2008.

(Continued)

*Primary Examiner* — Max Hindenburg
*Assistant Examiner* — Devin Henson

(57) ABSTRACT

A surgical instrument can be used to capture and retrieve tissue, or other specimens, from within the body of a patient through a single trocar port. The surgical instrument can include a grasper, wherein the grasper can be configured to capture a specimen, and a specimen retrieval bag, wherein the specimen retrieval bag can be configured to at least partially surround, or encapsulate, the captured specimen when the specimen retrieval bag is in a deployed position. In certain embodiments, the retrieval bag can be inverted as it is moved between undeployed and deployed positions. In various embodiments, the surgical instrument can further include a snare operably engaged with the specimen retrieval bag, wherein the snare can be configured to at least partially close the bag. A vacuum can be placed in communication with the bag to reduce the size of the bag before it is removed from the surgical site.

17 Claims, 7 Drawing Sheets

U.S. PATENT DOCUMENTS

| | | |
|---|---|---|
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,977,887 A | 12/1990 | Gouda |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A * | 3/1993 | Wetter et al. ............... 606/114 |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A * | 12/1994 | Graber et al. ............... 606/127 |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,449,021 A | 9/1995 | Chikama |

| | | | | | | |
|---|---|---|---|---|---|---|
| 5,456,667 A | 10/1995 | Ham et al. | | 5,730,740 A | 3/1998 | Wales et al. |
| 5,456,684 A | 10/1995 | Schmidt et al. | | 5,741,278 A | 4/1998 | Stevens |
| 5,458,131 A | 10/1995 | Wilk | | 5,741,285 A | 4/1998 | McBrayer et al. |
| 5,458,583 A | 10/1995 | McNeely et al. | | 5,746,759 A | 5/1998 | Meade et al. |
| 5,460,168 A | 10/1995 | Masubuchi et al. | | 5,749,881 A | 5/1998 | Sackier et al. |
| 5,460,629 A | 10/1995 | Shlain et al. | | 5,749,889 A | 5/1998 | Bacich et al. |
| 5,462,561 A | 10/1995 | Voda | | 5,752,951 A | 5/1998 | Yanik |
| 5,465,731 A | 11/1995 | Bell et al. | | 5,755,731 A | 5/1998 | Grinberg |
| 5,467,763 A | 11/1995 | McMahon et al. | | 5,766,167 A | 6/1998 | Eggers et al. |
| 5,468,250 A | 11/1995 | Paraschac et al. | | 5,766,170 A | 6/1998 | Eggers |
| 5,470,308 A | 11/1995 | Edwards et al. | | 5,766,205 A | 6/1998 | Zvenyatsky et al. |
| 5,470,320 A | 11/1995 | Tiefenbrun et al. | | 5,769,849 A | 6/1998 | Eggers |
| 5,478,347 A | 12/1995 | Aranyi | | 5,779,701 A | 7/1998 | McBrayer et al. |
| 5,480,404 A | 1/1996 | Kammerer et al. | | 5,779,716 A | 7/1998 | Cano et al. |
| 5,482,054 A | 1/1996 | Slater et al. | | 5,779,727 A | 7/1998 | Orejola |
| 5,484,451 A | 1/1996 | Akopov et al. | | 5,782,859 A | 7/1998 | Nicholas et al. |
| 5,489,256 A | 2/1996 | Adair | | 5,782,866 A | 7/1998 | Wenstrom, Jr. |
| 5,496,347 A | 3/1996 | Hashiguchi et al. | | 5,791,022 A | 8/1998 | Bohman |
| 5,499,990 A | 3/1996 | Schülken et al. | | 5,792,113 A | 8/1998 | Kramer et al. |
| 5,499,992 A | 3/1996 | Meade et al. | | 5,792,153 A | 8/1998 | Swain et al. |
| 5,501,692 A | 3/1996 | Riza | | 5,792,165 A | 8/1998 | Klieman et al. |
| 5,503,616 A | 4/1996 | Jones | | 5,797,835 A | 8/1998 | Green |
| 5,505,686 A | 4/1996 | Willis et al. | | 5,797,928 A | 8/1998 | Kogasaka |
| 5,507,755 A | 4/1996 | Gresl et al. | | 5,797,939 A | 8/1998 | Yoon |
| 5,511,564 A | 4/1996 | Wilk | | 5,797,941 A | 8/1998 | Schulze et al. |
| 5,514,157 A | 5/1996 | Nicholas et al. | | 5,803,903 A | 9/1998 | Athas et al. |
| 5,522,829 A | 6/1996 | Michalos | | 5,808,665 A | 9/1998 | Green |
| 5,522,830 A | 6/1996 | Aranyi | | 5,810,806 A | 9/1998 | Ritchart et al. |
| 5,527,321 A | 6/1996 | Hinchliffe | | 5,810,849 A | 9/1998 | Kontos |
| 5,540,648 A | 7/1996 | Yoon | | 5,810,865 A | 9/1998 | Koscher et al. |
| 5,554,151 A | 9/1996 | Hinchliffe | | 5,810,876 A | 9/1998 | Kelleher |
| 5,555,883 A | 9/1996 | Avitall | | 5,810,877 A | 9/1998 | Roth et al. |
| 5,558,133 A | 9/1996 | Bortoli et al. | | 5,813,976 A | 9/1998 | Filipi et al. |
| 5,562,693 A | 10/1996 | Devlin et al. | | 5,814,058 A | 9/1998 | Carlson et al. |
| 5,569,243 A | 10/1996 | Kortenbach et al. | | 5,817,061 A | 10/1998 | Goodwin et al. |
| 5,569,298 A | 10/1996 | Schnell | | 5,817,107 A | 10/1998 | Schaller |
| 5,573,540 A | 11/1996 | Yoon | | 5,817,119 A | 10/1998 | Klieman et al. |
| 5,578,030 A | 11/1996 | Levin | | 5,819,736 A | 10/1998 | Avny et al. |
| 5,582,611 A | 12/1996 | Tsuruta et al. | | 5,827,281 A | 10/1998 | Levin |
| 5,582,617 A | 12/1996 | Klieman et al. | | 5,827,299 A | 10/1998 | Thomason et al. |
| 5,584,845 A | 12/1996 | Hart | | 5,830,231 A | 11/1998 | Geiges, Jr. |
| 5,591,179 A | 1/1997 | Edelstein | | 5,833,700 A | 11/1998 | Fogelberg et al. |
| 5,593,420 A | 1/1997 | Eubanks, Jr et al. | | 5,833,703 A | 11/1998 | Manushakian |
| 5,595,562 A | 1/1997 | Grier | | 5,843,017 A | 12/1998 | Yoon |
| 5,597,378 A | 1/1997 | Jervis | | 5,849,022 A | 12/1998 | Sakashita et al. |
| 5,601,573 A | 2/1997 | Fogelberg et al. | | 5,853,374 A * | 12/1998 | Hart et al. ............ 600/562 |
| 5,601,588 A | 2/1997 | Tonomura et al. | | 5,855,585 A | 1/1999 | Kontos |
| 5,604,531 A | 2/1997 | Iddan et al. | | 5,860,913 A | 1/1999 | Yamaya et al. |
| 5,607,389 A | 3/1997 | Edwards et al. | | 5,860,995 A | 1/1999 | Berkelaar |
| 5,607,450 A | 3/1997 | Zvenyatsky et al. | | 5,868,762 A | 2/1999 | Cragg et al. |
| 5,613,975 A | 3/1997 | Christy | | 5,876,411 A | 3/1999 | Kontos |
| 5,618,303 A | 4/1997 | Marlow et al. | | 5,882,331 A | 3/1999 | Sasaki |
| 5,620,415 A | 4/1997 | Lucey et al. | | 5,882,344 A | 3/1999 | Stouder, Jr. |
| 5,624,399 A | 4/1997 | Ackerman | | 5,893,846 A | 4/1999 | Bales et al. |
| 5,624,431 A | 4/1997 | Gerry et al. | | 5,893,874 A | 4/1999 | Bourque et al. |
| 5,628,732 A | 5/1997 | Antoon, Jr. et al. | | 5,893,875 A | 4/1999 | O'Connor et al. |
| 5,630,782 A | 5/1997 | Adair | | 5,899,919 A | 5/1999 | Eubanks, Jr. et al. |
| 5,643,283 A * | 7/1997 | Younker ............ 606/17 | | 5,902,254 A | 5/1999 | Magram |
| 5,643,292 A | 7/1997 | Hart | | 5,904,702 A | 5/1999 | Ek et al. |
| 5,643,294 A | 7/1997 | Tovey et al. | | 5,908,420 A | 6/1999 | Parins et al. |
| 5,644,798 A | 7/1997 | Shah | | 5,916,147 A | 6/1999 | Boury |
| 5,645,083 A * | 7/1997 | Essig et al. ............ 128/898 | | 5,921,993 A | 7/1999 | Yoon |
| 5,649,372 A | 7/1997 | Souza | | 5,921,997 A | 7/1999 | Fogelberg et al. |
| 5,653,677 A | 8/1997 | Okada et al. | | 5,922,008 A | 7/1999 | Gimpelson |
| 5,653,722 A | 8/1997 | Kieturakis | | 5,925,052 A | 7/1999 | Simmons |
| 5,662,663 A | 9/1997 | Shallman | | 5,928,255 A | 7/1999 | Meade et al. |
| 5,669,875 A | 9/1997 | van Eerdenburg | | 5,928,266 A | 7/1999 | Kontos |
| 5,681,324 A | 10/1997 | Kammerer et al. | | 5,936,536 A | 8/1999 | Morris |
| 5,681,330 A | 10/1997 | Hughett et al. | | 5,944,718 A | 8/1999 | Austin et al. |
| 5,685,820 A | 11/1997 | Riek et al. | | 5,951,549 A | 9/1999 | Richardson et al. |
| 5,690,656 A | 11/1997 | Cope et al. | | 5,954,720 A | 9/1999 | Wilson et al. |
| 5,690,660 A | 11/1997 | Kauker et al. | | 5,954,731 A | 9/1999 | Yoon |
| 5,695,448 A | 12/1997 | Kimura et al. | | 5,957,943 A | 9/1999 | Vaitekunas |
| 5,695,505 A | 12/1997 | Yoon | | 5,957,953 A | 9/1999 | DiPoto et al. |
| 5,695,511 A | 12/1997 | Cano et al. | | 5,971,995 A | 10/1999 | Rousseau |
| 5,700,275 A | 12/1997 | Bell et al. | | 5,976,074 A | 11/1999 | Moriyama |
| 5,704,892 A | 1/1998 | Adair | | 5,976,075 A | 11/1999 | Beane et al. |
| 5,709,708 A | 1/1998 | Thal | | 5,976,130 A | 11/1999 | McBrayer et al. |
| 5,716,326 A | 2/1998 | Dannan | | 5,976,131 A | 11/1999 | Guglielmi et al. |

| | | | |
|---|---|---|---|
| 5,980,539 A | 11/1999 | Kontos | |
| 5,980,556 A | 11/1999 | Giordano et al. | |
| 5,984,938 A | 11/1999 | Yoon | |
| 5,989,182 A | 11/1999 | Hori et al. | |
| 5,993,447 A | 11/1999 | Blewett et al. | |
| 5,997,555 A | 12/1999 | Kontos | |
| 6,001,120 A | 12/1999 | Levin | |
| 6,004,330 A | 12/1999 | Middleman et al. | |
| 6,007,566 A | 12/1999 | Wenstrom, Jr. | |
| 6,010,515 A | 1/2000 | Swain et al. | |
| 6,012,494 A | 1/2000 | Balazs | |
| 6,019,770 A | 2/2000 | Christoudias | |
| 6,024,708 A | 2/2000 | Bales et al. | |
| 6,024,747 A | 2/2000 | Kontos | |
| 6,027,522 A | 2/2000 | Palmer | |
| 6,030,365 A | 2/2000 | Laufer | |
| 6,033,399 A | 3/2000 | Gines | |
| 6,053,927 A | 4/2000 | Hamas | |
| 6,066,160 A | 5/2000 | Colvin et al. | |
| 6,068,603 A | 5/2000 | Suzuki | |
| 6,068,629 A | 5/2000 | Haissaguerre et al. | |
| 6,071,233 A | 6/2000 | Ishikawa et al. | |
| 6,074,408 A | 6/2000 | Freeman | |
| 6,086,530 A | 7/2000 | Mack | |
| 6,090,108 A | 7/2000 | McBrayer et al. | |
| 6,096,046 A | 8/2000 | Weiss | |
| 6,110,154 A | 8/2000 | Shimomura et al. | |
| 6,110,183 A | 8/2000 | Cope | |
| 6,113,593 A | 9/2000 | Tu et al. | |
| 6,117,144 A | 9/2000 | Nobles et al. | |
| 6,117,158 A | 9/2000 | Measamer et al. | |
| 6,139,555 A | 10/2000 | Hart et al. | |
| 6,146,391 A | 11/2000 | Cigaina | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1 | 5/2001 | Marchand | |
| 6,245,079 B1 | 6/2001 | Nobles et al. | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,543 B1 | 3/2002 | Cole | |
| 6,355,035 B1 | 3/2002 | Manushakian | |
| 6,371,956 B1 | 4/2002 | Wilson et al. | |
| 6,379,366 B1 | 4/2002 | Fleischman et al. | |
| 6,383,195 B1 * | 5/2002 | Richard | 606/114 |
| 6,383,197 B1 | 5/2002 | Conlon et al. | |
| 6,391,029 B1 | 5/2002 | Hooven et al. | |
| 6,402,735 B1 | 6/2002 | Langevin | |
| 6,406,440 B1 | 6/2002 | Stefanchik | |
| 6,409,733 B1 | 6/2002 | Conlon et al. | |
| 6,431,500 B1 | 8/2002 | Jacobs et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,464,701 B1 | 10/2002 | Hooven et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,691 B1 | 12/2002 | Morley et al. | |
| 6,493,590 B1 | 12/2002 | Wessman et al. | |
| 6,494,893 B2 | 12/2002 | Dubrul et al. | |
| 6,503,192 B1 | 1/2003 | Ouchi | |
| 6,506,190 B1 | 1/2003 | Walshe | |
| 6,508,827 B1 | 1/2003 | Manhes | |
| 6,543,456 B1 | 4/2003 | Freeman | |
| 6,551,270 B1 | 4/2003 | Bimbo et al. | |
| 6,554,829 B2 | 4/2003 | Schulze et al. | |
| 6,558,384 B2 | 5/2003 | Mayenberger | |
| 6,562,035 B1 | 5/2003 | Levin | |
| 6,562,052 B2 | 5/2003 | Nobles et al. | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,579,311 B1 | 6/2003 | Makower | |
| 6,585,642 B2 | 7/2003 | Christopher | |
| 6,585,717 B1 | 7/2003 | Wittenberger et al. | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,626,919 B1 | 9/2003 | Swanstrom | |
| 6,632,229 B1 | 10/2003 | Yamanouchi | |
| 6,638,286 B1 | 10/2003 | Burbank et al. | |
| 6,652,521 B2 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,666,854 B1 | 12/2003 | Lange | |
| 6,672,338 B1 | 1/2004 | Esashi et al. | |
| 6,673,087 B1 | 1/2004 | Chang et al. | |
| 6,685,628 B2 | 2/2004 | Vu | |
| 6,685,724 B1 | 2/2004 | Haluck | |
| 6,692,445 B2 | 2/2004 | Roberts et al. | |
| 6,692,462 B2 | 2/2004 | Mackenzie et al. | |
| 6,699,180 B2 | 3/2004 | Kobayashi | |
| 6,699,256 B1 | 3/2004 | Logan et al. | |
| 6,699,263 B2 | 3/2004 | Cope | |
| 6,708,066 B2 | 3/2004 | Herbst et al. | |
| 6,716,226 B2 | 4/2004 | Sixto, Jr. et al. | |
| 6,740,030 B2 | 5/2004 | Martone et al. | |
| 6,743,240 B2 | 6/2004 | Smith et al. | |
| 6,749,560 B1 | 6/2004 | Konstorum et al. | |
| 6,749,609 B1 | 6/2004 | Lunsford et al. | |
| 6,752,768 B2 | 6/2004 | Burdorff et al. | |
| 6,752,811 B2 | 6/2004 | Chu et al. | |
| 6,752,822 B2 * | 6/2004 | Jespersen | 606/205 |
| 6,761,685 B2 | 7/2004 | Adams et al. | |
| 6,761,718 B2 | 7/2004 | Madsen | |
| 6,761,722 B2 | 7/2004 | Cole et al. | |
| 6,773,434 B2 | 8/2004 | Ciarrocca | |
| 6,780,151 B2 | 8/2004 | Grabover et al. | |
| 6,780,352 B2 | 8/2004 | Jacobson | |
| 6,783,491 B2 | 8/2004 | Saadat et al. | |
| 6,786,864 B2 | 9/2004 | Matsuura et al. | |
| 6,790,173 B2 | 9/2004 | Saadat et al. | |
| 6,795,728 B2 | 9/2004 | Chornenky et al. | |
| 6,800,056 B2 | 10/2004 | Tartaglia et al. | |
| 6,808,491 B2 | 10/2004 | Kortenbach et al. | |
| 6,824,548 B2 | 11/2004 | Smith et al. | |
| 6,837,847 B2 | 1/2005 | Ewers et al. | |
| 6,843,794 B2 | 1/2005 | Sixto, Jr. et al. | |
| 6,861,250 B1 | 3/2005 | Cole et al. | |
| 6,866,627 B2 | 3/2005 | Nozue | |
| 6,878,106 B1 | 4/2005 | Herrmann | |

| | | |
|---|---|---|
| 6,878,110 B2 | 4/2005 | Yang et al. |
| 6,884,213 B2 | 4/2005 | Raz et al. |
| 6,887,255 B2 | 5/2005 | Shimm |
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,222 B2 | 7/2008 | Asakura |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |

| | | |
|---|---|---|
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0242960 A1* | 12/2004 | Orban, III ................... 600/106 |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1* | 9/2005 | Sepetka et al. ................. 606/200 |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1* | 2/2006 | Young et al. ................... 606/114 |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |
| 2006/0079890 A1 | 4/2006 | Guerra |
| 2006/0089528 A1 | 4/2006 | Tartaglia et al. |

| | | | | | |
|---|---|---|---|---|---|
| 2006/0095060 A1 | 5/2006 | Mayenberger et al. | 2007/0100376 A1 | 5/2007 | Mikkaichi et al. |
| 2006/0100687 A1 | 5/2006 | Fahey et al. | 2007/0106118 A1 | 5/2007 | Moriyama |
| 2006/0106423 A1 | 5/2006 | Weisel et al. | 2007/0112251 A1 | 5/2007 | Nakhuda |
| 2006/0111209 A1 | 5/2006 | Hinman et al. | 2007/0112331 A1 | 5/2007 | Weber et al. |
| 2006/0111210 A1 | 5/2006 | Hinman et al. | 2007/0112342 A1 | 5/2007 | Pearson et al. |
| 2006/0111704 A1 | 5/2006 | Brenneman et al. | 2007/0112383 A1 | 5/2007 | Conlon et al. |
| 2006/0129166 A1 | 6/2006 | Lavelle | 2007/0112384 A1 | 5/2007 | Conlon et al. |
| 2006/0135962 A1 | 6/2006 | Kick et al. | 2007/0112385 A1 | 5/2007 | Conlon |
| 2006/0135971 A1 | 6/2006 | Swanstrom et al. | 2007/0112417 A1 | 5/2007 | Shanley et al. |
| 2006/0135984 A1 | 6/2006 | Kramer et al. | 2007/0112425 A1 | 5/2007 | Schaller et al. |
| 2006/0142644 A1 | 6/2006 | Mulac et al. | 2007/0118115 A1 | 5/2007 | Artale et al. |
| 2006/0142652 A1 | 6/2006 | Keenan | 2007/0123840 A1 | 5/2007 | Cox |
| 2006/0142790 A1 | 6/2006 | Gertner | 2007/0129605 A1 | 6/2007 | Schaaf |
| 2006/0142798 A1 | 6/2006 | Holman et al. | 2007/0129719 A1 | 6/2007 | Kendale et al. |
| 2006/0149132 A1 | 7/2006 | Iddan | 2007/0135709 A1 | 6/2007 | Rioux et al. |
| 2006/0149135 A1 | 7/2006 | Paz | 2007/0142706 A1 | 6/2007 | Matsui et al. |
| 2006/0161190 A1 | 7/2006 | Gadberry et al. | 2007/0156127 A1 | 7/2007 | Rioux et al. |
| 2006/0167416 A1 | 7/2006 | Mathis et al. | 2007/0161855 A1 | 7/2007 | Mikkaichi et al. |
| 2006/0167482 A1 | 7/2006 | Swain et al. | 2007/0173691 A1 | 7/2007 | Yokoi et al. |
| 2006/0178560 A1 | 8/2006 | Saadat et al. | 2007/0173869 A1 | 7/2007 | Gannoe et al. |
| 2006/0183975 A1 | 8/2006 | Saadat et al. | 2007/0173870 A2 | 7/2007 | Zacharias |
| 2006/0184161 A1 | 8/2006 | Maahs et al. | 2007/0173872 A1 | 7/2007 | Neuenfeldt |
| 2006/0189844 A1 | 8/2006 | Tien | 2007/0179525 A1 | 8/2007 | Frecker et al. |
| 2006/0189845 A1 | 8/2006 | Maahs et al. | 2007/0179530 A1 | 8/2007 | Tieu et al. |
| 2006/0190027 A1 | 8/2006 | Downey | 2007/0197865 A1 | 8/2007 | Miyake et al. |
| 2006/0195084 A1 | 8/2006 | Slater | 2007/0203487 A1 | 8/2007 | Sugita |
| 2006/0200005 A1 | 9/2006 | Bjork et al. | 2007/0208364 A1 | 9/2007 | Smith et al. |
| 2006/0200169 A1 | 9/2006 | Sniffin | 2007/0213754 A1 | 9/2007 | Mikkaichi et al. |
| 2006/0200170 A1 | 9/2006 | Aranyi | 2007/0225554 A1 | 9/2007 | Maseda et al. |
| 2006/0200199 A1 | 9/2006 | Bonutti et al. | 2007/0233040 A1 | 10/2007 | Macnamara et al. |
| 2006/0217665 A1 | 9/2006 | Prosek | 2007/0244358 A1 | 10/2007 | Lee |
| 2006/0217697 A1 | 9/2006 | Lau et al. | 2007/0250057 A1 | 10/2007 | Nobis et al. |
| 2006/0217742 A1 | 9/2006 | Messerly et al. | 2007/0255096 A1 | 11/2007 | Stefanchik et al. |
| 2006/0217743 A1 | 9/2006 | Messerly et al. | 2007/0255100 A1 | 11/2007 | Barlow et al. |
| 2006/0229639 A1 | 10/2006 | Whitfield | 2007/0255273 A1 | 11/2007 | Fernandez et al. |
| 2006/0229640 A1 | 10/2006 | Whitfield | 2007/0255303 A1 | 11/2007 | Bakos et al. |
| 2006/0237022 A1 | 10/2006 | Chen et al. | 2007/0255306 A1 | 11/2007 | Conlon et al. |
| 2006/0237023 A1 | 10/2006 | Cox et al. | 2007/0260112 A1 | 11/2007 | Rahmani |
| 2006/0241570 A1 | 10/2006 | Wilk | 2007/0260117 A1 | 11/2007 | Zwolinski et al. |
| 2006/0247576 A1 | 11/2006 | Poncet | 2007/0260121 A1 | 11/2007 | Bakos et al. |
| 2006/0247673 A1 | 11/2006 | Voegele et al. | 2007/0260273 A1 | 11/2007 | Cropper et al. |
| 2006/0253004 A1 | 11/2006 | Frisch et al. | 2007/0270629 A1 | 11/2007 | Charles |
| 2006/0253039 A1 | 11/2006 | McKenna et al. | 2007/0270889 A1 | 11/2007 | Conlon et al. |
| 2006/0258907 A1 | 11/2006 | Stefanchik et al. | 2007/0270895 A1 | 11/2007 | Nobis et al. |
| 2006/0258908 A1 | 11/2006 | Stefanchik et al. | 2007/0270907 A1 | 11/2007 | Stokes et al. |
| 2006/0258910 A1 | 11/2006 | Stefanchik et al. | 2007/0282371 A1 | 12/2007 | Lee et al. |
| 2006/0258954 A1 | 11/2006 | Timberlake et al. | 2007/0299387 A1 | 12/2007 | Williams et al. |
| 2006/0258955 A1 | 11/2006 | Hoffman et al. | 2008/0004650 A1 | 1/2008 | George |
| 2006/0259010 A1 | 11/2006 | Stefanchik et al. | 2008/0015409 A1 | 1/2008 | Barlow et al. |
| 2006/0264752 A1 | 11/2006 | Rubinsky et al. | 2008/0015552 A1 | 1/2008 | Doyle et al. |
| 2006/0264904 A1 | 11/2006 | Kerby et al. | 2008/0027387 A1 | 1/2008 | Grabinsky |
| 2006/0264930 A1 | 11/2006 | Nishimura | 2008/0033451 A1 | 2/2008 | Rieber et al. |
| 2006/0270902 A1 | 11/2006 | Igarashi et al. | 2008/0051629 A1 | 2/2008 | Sugiyama et al. |
| 2006/0271102 A1 | 11/2006 | Bosshard et al. | 2008/0051735 A1 | 2/2008 | Measamer et al. |
| 2006/0276835 A1 | 12/2006 | Uchida | 2008/0058586 A1 | 3/2008 | Karpiel |
| 2006/0281970 A1 | 12/2006 | Stokes et al. | 2008/0065169 A1 | 3/2008 | Colliou et al. |
| 2006/0282106 A1 | 12/2006 | Cole et al. | 2008/0086172 A1 | 4/2008 | Martin et al. |
| 2006/0285732 A1 | 12/2006 | Horn et al. | 2008/0097472 A1 | 4/2008 | Agmon et al. |
| 2006/0287644 A1 | 12/2006 | Inganas et al. | 2008/0097483 A1 | 4/2008 | Ortiz et al. |
| 2006/0287666 A1 | 12/2006 | Saadat et al. | 2008/0103527 A1 | 5/2008 | Martin et al. |
| 2006/0293626 A1 | 12/2006 | Byrum et al. | 2008/0114384 A1 | 5/2008 | Chang et al. |
| 2007/0002135 A1 | 1/2007 | Glukhovsky | 2008/0119870 A1 | 5/2008 | Williams |
| 2007/0005019 A1 | 1/2007 | Okishige | 2008/0125796 A1 | 5/2008 | Graham |
| 2007/0015965 A1 | 1/2007 | Cox et al. | 2008/0132892 A1 | 6/2008 | Lunsford et al. |
| 2007/0016225 A1 | 1/2007 | Nakao | 2008/0139882 A1 | 6/2008 | Fujimori |
| 2007/0032700 A1 | 2/2007 | Fowler et al. | 2008/0147113 A1 | 6/2008 | Nobis et al. |
| 2007/0032701 A1 | 2/2007 | Fowler et al. | 2008/0171907 A1 | 7/2008 | Long et al. |
| 2007/0043261 A1 | 2/2007 | Watanabe et al. | 2008/0188868 A1 | 8/2008 | Weitzner et al. |
| 2007/0043345 A1 | 2/2007 | Davalos et al. | 2008/0200755 A1 | 8/2008 | Bakos |
| 2007/0049800 A1 | 3/2007 | Boulais | 2008/0200762 A1 | 8/2008 | Stokes et al. |
| 2007/0049902 A1 | 3/2007 | Griffin et al. | 2008/0200911 A1 | 8/2008 | Long |
| 2007/0051375 A1 | 3/2007 | Milliman | 2008/0200912 A1 | 8/2008 | Long |
| 2007/0060880 A1 | 3/2007 | Gregorich et al. | 2008/0200933 A1 | 8/2008 | Bakos et al. |
| 2007/0067017 A1 | 3/2007 | Trapp | 2008/0200934 A1 | 8/2008 | Fox |
| 2007/0073102 A1 | 3/2007 | Matsuno et al. | 2008/0208213 A1 | 8/2008 | Benjamin et al. |
| 2007/0073269 A1 | 3/2007 | Becker | 2008/0221587 A1 | 9/2008 | Schwartz |
| 2007/0079924 A1 | 4/2007 | Saadat et al. | 2008/0221619 A1 | 9/2008 | Spivey et al. |
| 2007/0088370 A1 | 4/2007 | Kahle et al. | 2008/0228213 A1 | 9/2008 | Blakeney et al. |
| 2007/0100375 A1 | 5/2007 | Mikkaichi et al. | 2008/0230972 A1 | 9/2008 | Ganley |

| | | |
|---|---|---|
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1* | 12/2008 | Zwolinski ............... 600/104 |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwollinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |

| | | |
|---|---|---|
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |
| FR | 2731610 A1 | 9/1996 |
| GB | 330629 A | 6/1930 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2010/088481 A1 | 8/2010 |

OTHER PUBLICATIONS

Michael S. Kavic, M.D., "Natural Orifice Translumenal Endoscopic Surgery: "Notes"", JSLS, vol. 10, pp. 133-134 (2006).

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey Notes Presentation to EES Notes Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastomosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastomotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/ Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. (2007), pp. 255-259.

D.B. Nelson, MD et al., "Endoscopic Hemostatic Devices," Gastrointestinal Endoscopy, vol. 54, No. 6, 2001, pp. 833-840.

Cre™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 12/277,975, filed Nov. 25, 2008.
U.S. Appl. No. 12/277,957, filed Nov. 25, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.

D. Wilhelm et al., "An Innovative, Safe and Sterile Sigmoid Access (ISSA) for Notes," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavöiö et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation in Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal Notes Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked Ni-Ti," Engineering Aspects of Shape Memory Alloys, pp. 414-419.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/694,452, filed Jan. 27, 2010.
U.S. Appl. No. 12/752,701, filed Apr. 1, 2010.
Zadno et al., "Linear Superelasticity in Cold-Worked Ni-Ti," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

* cited by examiner

SPECIMEN RETRIEVAL DEVICE

BACKGROUND i. Field of the Invention

The present invention generally relates to surgical devices and, more particularly, to surgical devices for capturing and retrieving tissue from within a patient's body.

ii. Description of the Related Art

Traditional, or open, surgical techniques may require a surgeon to make large incisions in a patient's body in order to access a tissue treatment region, or surgical site. In some instances, these large incisions may prolong the recovery time of and/or increase the scarring to the patient. As a result, minimally invasive surgical techniques are becoming more preferred among surgeons and patients owing to the reduced size of the incisions required for various procedures. In some circumstances, minimally invasive surgical techniques may reduce the possibility that the patient will suffer undesirable post-surgical conditions, such as scarring and/or infections, for example. Further, such minimally invasive techniques can allow the patient to recover more rapidly as compared to traditional surgical procedures.

Endoscopy is one minimally invasive surgical technique which allows a surgeon to view and evaluate a surgical site by inserting at least one cannula, or trocar, into the patient's body through a natural opening in the body and/or through a relatively small incision. In use, an endoscope can be inserted into, or through, the trocar so that the surgeon can observe the surgical site. In various embodiments, the endoscope may include a flexible or rigid shaft, a camera and/or other suitable optical device, and a handle portion. In at least one embodiment, the optical device can be located on a first, or distal, end of the shaft and the handle portion can be located on a second, or proximal, end of the shaft. In various embodiments, the endoscope may also be configured to assist a surgeon in taking biopsies, retrieving foreign objects, and introducing surgical instruments into the surgical site.

Laparoscopic surgery is another minimally invasive surgical technique where procedures in the abdominal or pelvic cavities can be performed through small incisions in the patient's body. A key element of laparoscopic surgery is the use of a laparoscope which typically includes a telescopic lens system that can be connected to a video camera. In various embodiments, a laparoscope can further include a fiber optic system connected to a halogen or xenon light source, for example, in order to illuminate the surgical site. In various laparoscopic, and/or endoscopic, surgical procedures, a body cavity of a patient, such as the abdominal cavity, for example, can be insufflated with carbon dioxide gas, for example, in order to create a temporary working space for the surgeon. In such procedures, a cavity wall can be elevated above the organs within the cavity by the carbon dioxide gas. Carbon dioxide gas is usually used for insufflation because it can be easily absorbed and removed by the body.

In at least one minimally invasive surgical procedure, an endoscope and/or laparoscope can be inserted through a natural opening of a patient to allow a surgeon to access a surgical site. Such procedures are generally referred to as Nature Orifice Transluminal Endoscopic Surgery or (NOTES)™ and can be utilized to treat tissue while reducing the number of incisions, and external scars, to a patient's body. In various NOTES procedures, for example, an endoscope can include at least one working channel defined therein which can be used to allow the surgeon to insert a surgical instrument therethrough in order to access the surgical site.

SUMMARY

According to at least one aspect, surgical instruments including a tissue holder and a specimen retrieval receptacle can be utilized to facilitate the capture and retrieval of a tissue specimen from a surgical site. In various embodiments, as described herein, such a surgical instrument can allow a surgeon to easily grasp and retrieve a specimen from a surgical site using a single trocar port, for example. In at least one embodiment, the surgical instrument can include a grasper, wherein the grasper can include one or more jaws which can be inserted through the trocar port. Once inserted therethrough, the jaws can be opened and closed, as needed, in order to capture tissue therebetween. A specimen retrieval bag can be slid relative to the grasper and positioned such that the specimen is at least partially surrounded by the specimen retrieval bag. In various embodiments, the surgical instrument can further include an actuator operably engaged with the specimen retrieval bag, wherein the actuator can be configured to move the specimen retrieval bag between undeployed and deployed positions. In certain embodiments, the actuator can comprise a snare loop which can be engaged with at least a portion of the perimeter of the specimen retrieval bag such that the snare loop can at least partially close the bag. Once the specimen retrieval bag has been suitably positioned and/or closed, the specimen retrieval bag can be removed from the surgical site though the trocar lumen. In at least one embodiment, the specimen retrieval bag and the grasper can be pulled through the trocar at the same time while, in other embodiments, the specimen retrieval bag and the grasper can be pulled through the trocar sequentially. In any event, in various embodiments, a specimen can be grasped, manipulated, and removed from a surgical site through a single trocar utilizing a single surgical instrument.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 1:
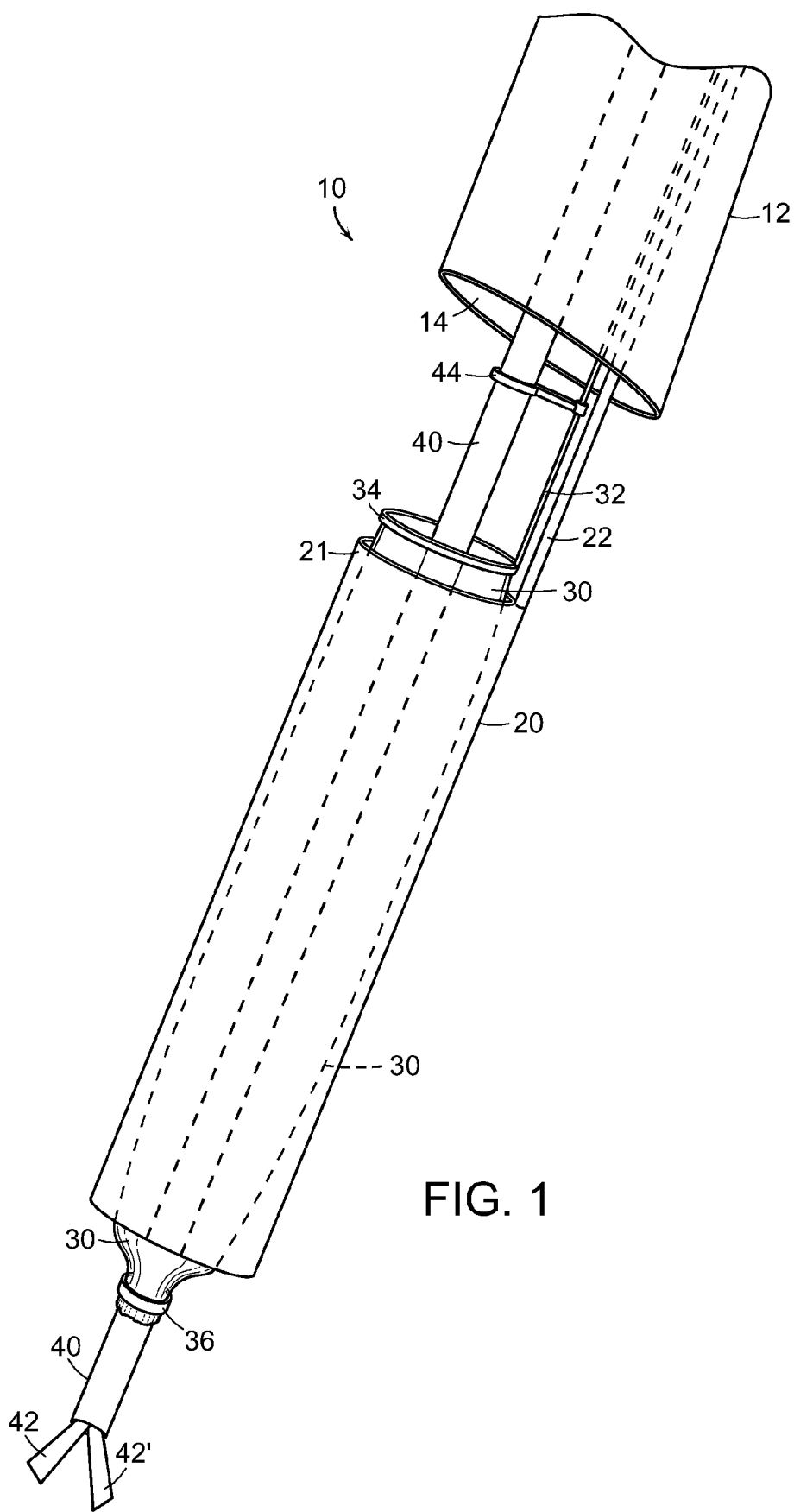
FIG. 1 is a diagram of a surgical instrument including an outer sheath, a specimen retrieval bag, and a grasper in accordance with one non-limiting embodiment of the present invention.

During the course of various surgical procedures, especially in intraluminal and transluminal procedures, there often exists a need to simultaneously introduce several surgical instruments into a surgical cavity, for example. Various surgical instruments include, for example, a grasper configured to gain control of a specimen and a specimen retrieval pouch configured to isolate and remove the specimen from the surgical cavity. According to various surgical procedures, a first trocar is inserted into the surgical cavity to introduce the grasper into the surgical cavity and, in addition, a second trocar is inserted into the surgical cavity to introduce the retrieval pouch into the surgical cavity.

Among the greatest difficulties in performing surgical procedures, especially in intraluminal and transluminal procedures, is limiting the number of peritoneal insults required to complete the surgical procedure. For example, intraluminal and transluminal procedures to retrieve tissue, or other specimens, from a peritoneal surgical site often incorporate the use of a grasper and a specimen retrieval bag, wherein each device is introduced through a separate trocar, and wherein each trocar can create an insult to a peritoneal cavity wall, for example. Stated another way, each additional trocar can introduce an additional peritoneal insult, thereby significantly increasing the time and complexity of the surgical procedure and, in addition, the risks for port site infection, herniation, and recovery time for the patient, for example.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

In various embodiments, a surgical instrument, and/or surgical instrument kit, can include components which can be configured to grasp and retrieve a specimen from within the body of a patient such that a surgeon can easily access, and retrieve a specimen within, a surgical site using a single surgical instrument. In at least one embodiment, referring to FIG. 1, a surgical instrument 10 can include several components, such as an outer sheath 20, a specimen retrieval bag 30, and a grasper 40, for example, which can be cooperatively utilized in order to easily grasp and retrieve a specimen from a surgical cavity through a single peritoneal insult. Other surgical instruments are disclosed in co-pending, commonly-owned U.S. patent application Ser. No. 12/133,109, entitled ENDOSCOPIC DROP OFF BAG, which was filed on Jun. 4, 2008, the entire disclosure of which is hereby incorporated by reference herein.

In various embodiments, as outlined above, the surgical instrument 10 can include a grasper 40, and/or any other suitable grasping device, for example. The grasper 40 can be cylindrical, at least substantially cylindrical, and/or any other suitable shape and can define a grasper lumen (not shown) extending along the length thereof. According to at least one embodiment, the grasper 40 can be an approximately 5 mm diameter grasper. In certain embodiments, the grasper 40 can include one or more grasper jaws, such as grasper jaws 42 and 42', for example. The grasper jaws 42 and 42' can be configured to be transitioned from an expanded, or open, position, where the interior distal tips of jaws 42 and 42' are apart from one another, to a collapsed, or closed, position, where the interior distal tips of jaws 42 and 42' are in contact with one another, or at least adjacent to one another, in order to capture a specimen therebetween. In at least one embodiment, the grasper jaws 42 and 42' can be configured to be slidably received within, and extendable from, the grasper lumen and, in various embodiments, grasper 40 can include suitable controls for manipulating grasper jaws 42 and 42'. In certain embodiments, a grasper can include a corkscrew, a hook, a vacuum source, a T-tag deployer and/or any other suitable device capable of capturing a specimen.

In various embodiments, as also outlined above, the surgical instrument 10 can include specimen retrieval bag 30 and/or any other suitable specimen receptacle, for example. In at least one embodiment, the distal end of the specimen retrieval bag 30 can be configured to be attached to the distal end of the grasper 40 by an attachment mechanism 36. In various embodiments, attachment mechanism 36 can comprise a closable device which can apply a compressive force to bag 30 and grasper 40, such as a zip tie, for example. In certain embodiments, retrieval bag 30 can be affixed to grasper 40 by an adhesive and/or a fastener, for example. In various embodiments, retrieval bag 30 can include a first end 31 affixed to grasper 40 and a second end 33 which can be moved relative to the first end 31. As will be described in greater detail below, the second end 33 of retrieval bag 30 can be repositioned such that retrieval bag 30 can at least partially cover or encapsulate the targeted specimen.

In various embodiments, further to the above, surgical instrument 10 can include an actuator operably engaged with retrieval bag 30, wherein the actuator can be configured to move second end 33 relative to first end 31. In at least one embodiment, the actuator can be affixed to second end 33 such that the actuator can be utilized to push second end 33 distally until second end 33 at least partially covers the targeted specimen. In certain embodiments, referring primarily to FIG. 1, the actuator can comprise a snare 32 having a snare loop 34 at least partially engaged with the perimeter of retrieval bag 30. In at least one embodiment, snare 32 can extend through trocar 12 alongside grasper 40 such that a surgeon can manipulate snare 32 and, accordingly, manipulate retrieval bag 30. In use, as described in greater detail below, snare 32 can be manipulated to extend the specimen retrieval bag 30 distally toward the grasper jaws 42 and 42', for example, and/or proximally away from the grasper jaws 42 and 42', for example. In certain embodiments, the snare 32 can be configured to pass through a coupler 44 associated with and/or extending from the grasper 40 such that snare 32 can be slidably guided by coupler 44. In at least one such embodiment, the coupler 44 can maintain the snare 32 in parallel alignment, or at least substantially parallel alignment, with the grasper 40.

Figure 2:
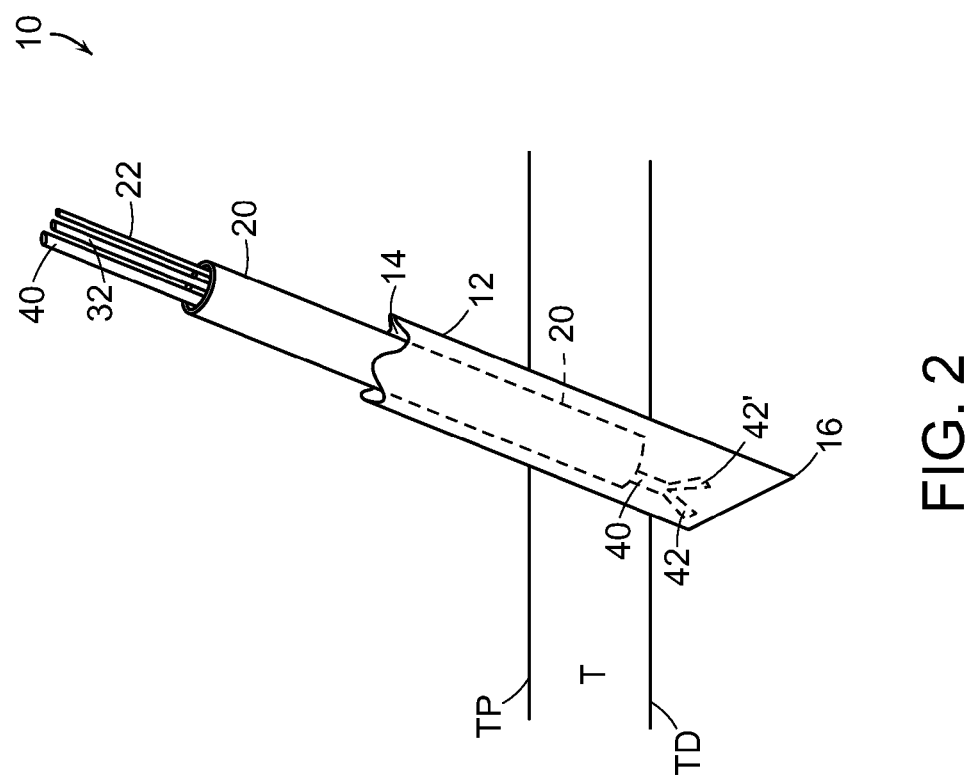
FIG. 2 is a diagram of the surgical instrument of FIG. 1 inserted through a trocar extending through a tissue wall in accordance with one non-limiting embodiment of the present invention.

In various embodiments, referring to FIGS. 1 and 2, the surgical instrument 10, and/or a kit including surgical instrument 10, for example, can further include a trocar, such as trocar 12, for example, which can be utilized to access the peritoneal cavity of a patient. The trocar 12 can be cylindrical, at least substantially cylindrical, and/or any other suitable shape and can define a trocar lumen 14 extending along at least a portion thereof. According to at least one embodiment, the trocar can be an approximately 10-12 mm diameter trocar. In certain embodiments, as described in greater detail below, the surgical instrument 10 can be configured to be slidably received within the trocar lumen 14 such that the grasper 40, specimen retrieval bag 30, and/or outer sheath 20 can be inserted into the surgical cavity.

In various embodiments, further to the above and referring to FIG. 2, trocar 12 can be inserted into a patient's body and advanced through a tissue wall "T". In at least one such embodiment, the distal tip 16 of trocar 12 can be advanced through the tissue wall T from the proximal tissue wall surface "TP" and beyond the distal tissue wall surface "TD". In certain embodiments, the distal tip 16 of trocar 12 can be configured to incise tissue wall T as it is inserted into a surgical cavity. In various embodiments, as outlined above, surgical instrument 10 can further include a sheath 20 which can be configured to cover at least a portion of specimen retrieval bag 30 and/or grasper 40, for example, as they are inserted through trocar 12. The sheath 20 can be cylindrical, at least substantially cylindrical, and/or any other suitable shape and can define a sheath lumen extending along the length thereof. In certain embodiments, outer sheath 20 can be formed of a rigid, or at least a substantially rigid, material and can be configured to maintain the position and integrity of the specimen retrieval bag 30, for example, as surgical instrument 10 is inserted through the trocar 12 and into the surgical cavity.

Figure 3:
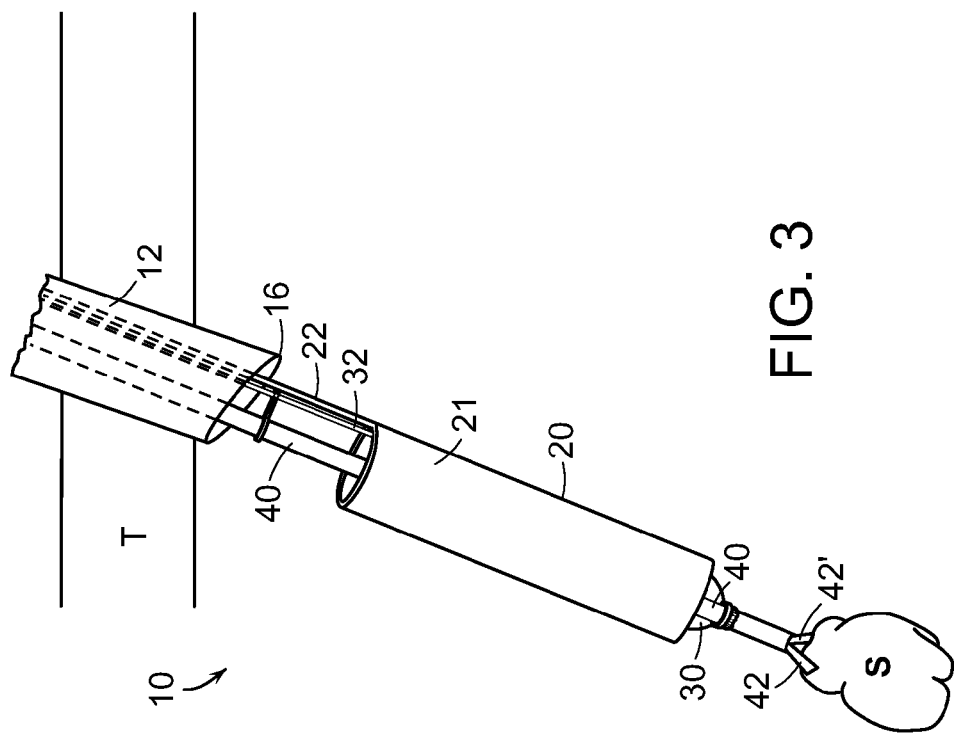
FIG. 3 is a diagram of the surgical instrument of FIG. 1 after the grasper, outer sheath, and specimen retrieval bag have been inserted into a surgical site.
Figure 5:
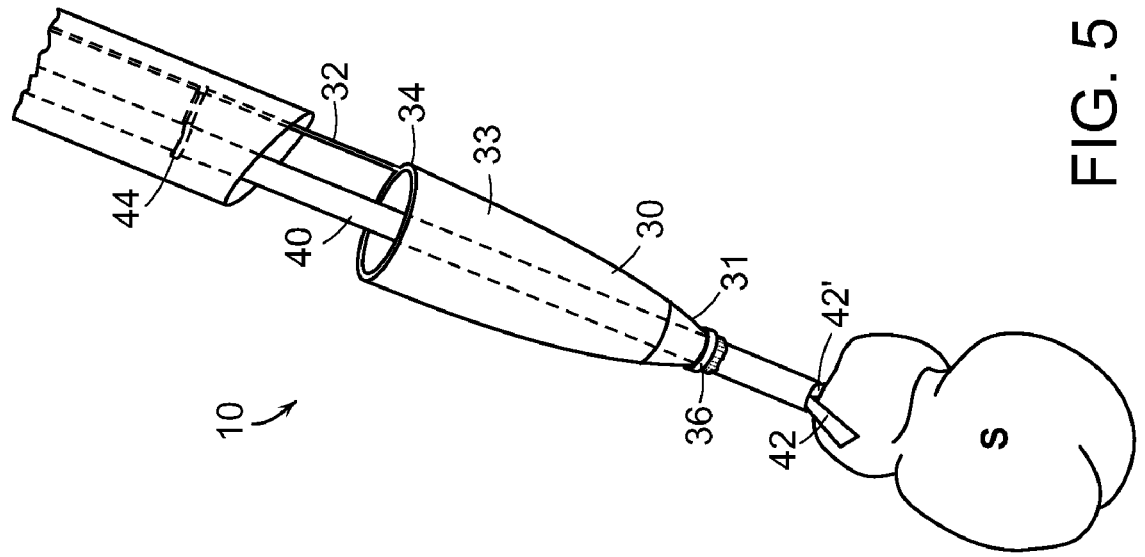
FIG. 5 is a diagram of the surgical instrument of FIG. 1 after the outer sheath has been retracted relative to the specimen retrieval bag and the grasper.
Figure 4:
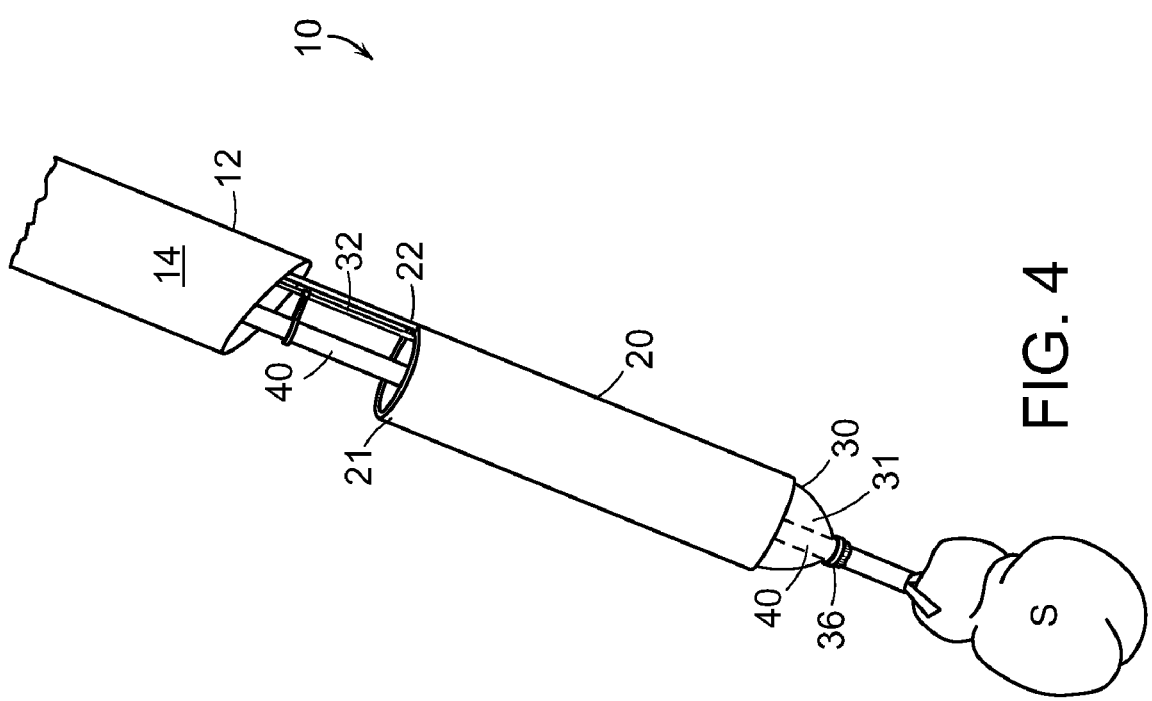
FIG. 4 is a diagram of the surgical instrument of FIG. 1 as the outer sheath is being retracted into the trocar.

In various embodiments, referring to FIG. 3, the outer sheath 20, specimen retrieval bag 30, and/or grasper 40 can be advanced through the trocar lumen 14 of trocar 12 and, accordingly, tissue wall T, until the proximal end 21 of the outer sheath 20 is positioned substantially beyond the distal end 16 of the trocar 12. In at least one embodiment, the surgical instrument 10 can be moved into the surgical cavity and the grasper jaws 42 and 42' can be brought into contact with the specimen "S" such that the specimen can be retrieved from the surgical cavity as described in greater detail below. Prior to, during, and/or subsequent to the capture of the specimen S, referring to FIG. 4, outer sheath 20 can be retracted proximally into the trocar lumen 14 of trocar 12 in order to expose the specimen retrieval bag 30. In at least one embodiment, outer sheath 20 can be retracted by a pull string, or ribbon, 22, and/or any other suitable device, attached to or otherwise operably engaged with outer sheath 20. As a result of the above, referring to FIG. 5, at least a portion of the specimen retrieval bag 30 and/or snare 32 can be exposed. In certain embodiments, snare loop 34 of snare 32 can be stored within sheath 20 such that, when sheath 20 is slid proximally, snare loop 34 can resiliently expand in order to open, or at least substantially open, second end 33 of retrieval bag 30. In some embodiments, snare 32 can be utilized to open and/or close snare loop 34 by expanding or contracting its diameter and/or circumference.

Figure 7:
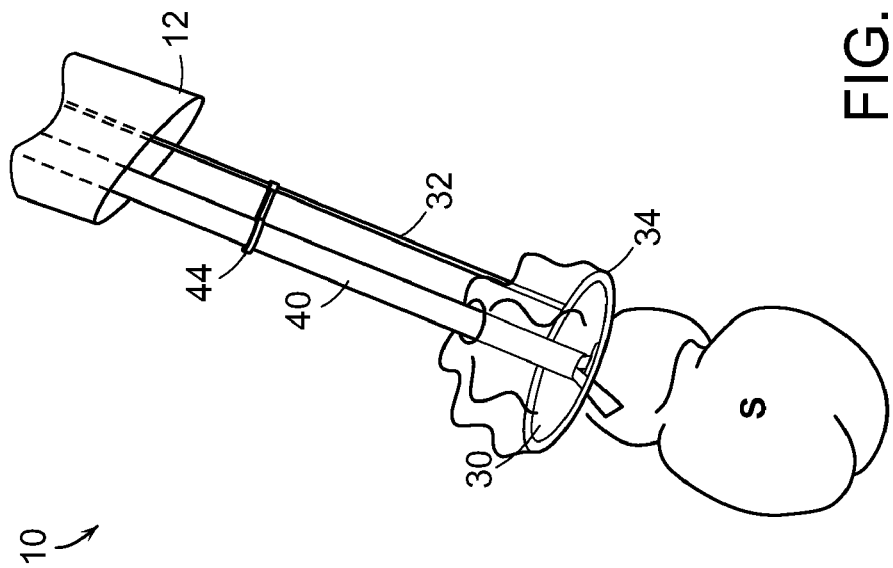
FIG. 7 is a diagram of the surgical instrument of FIG. 1 illustrating the specimen retrieval bag in a partially extended position.
Figure 6:
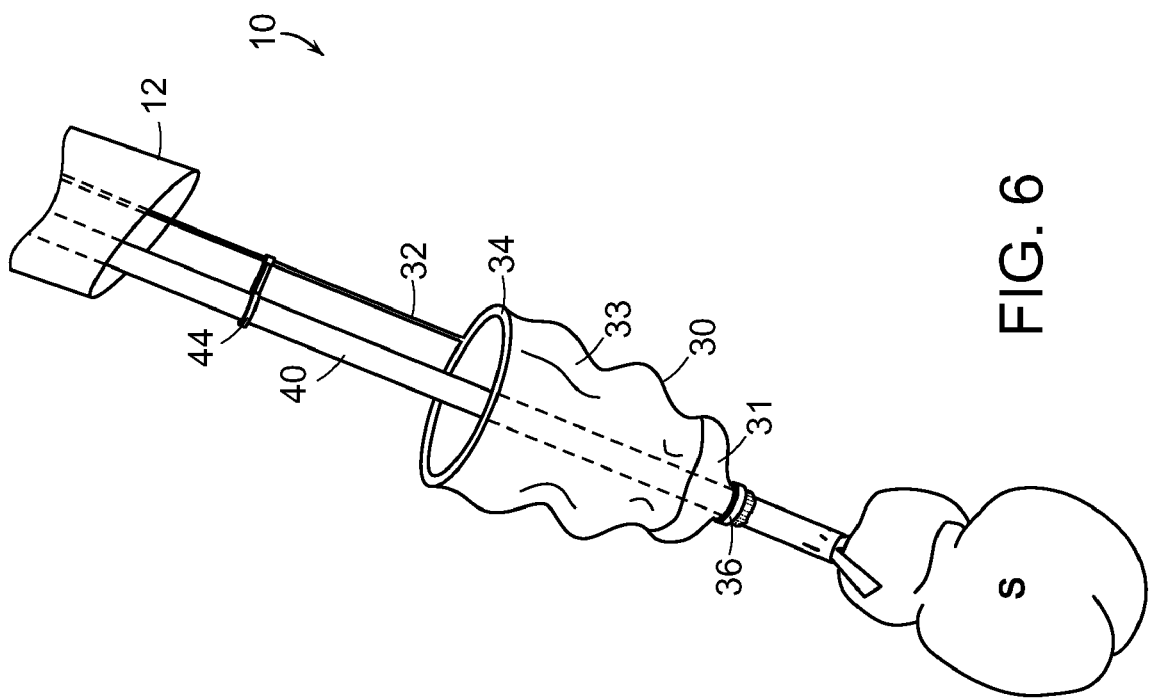
FIG. 6 is a diagram of the surgical instrument of FIG. 1 illustrating the specimen retrieval bag being extended distally by an actuator.
Figure 8:
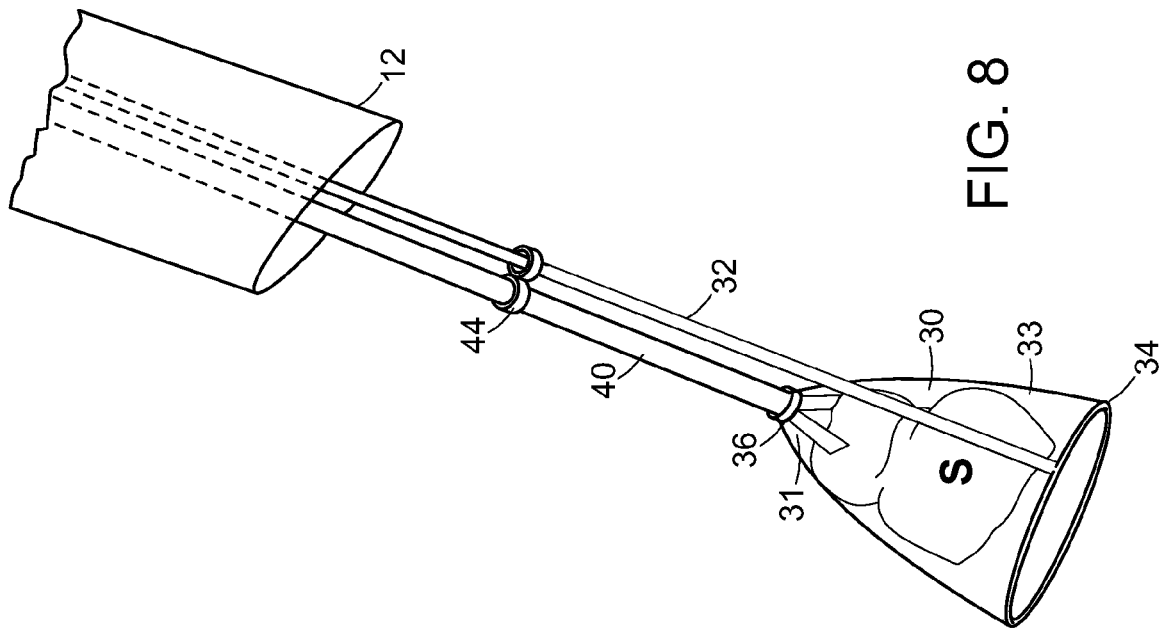
FIG. 8 is a diagram of the surgical instrument of FIG. 1 illustrating the specimen retrieval bag at least partially surrounding a tissue specimen.

In various embodiments, referring to FIG. 6, the second end 33 of specimen retrieval bag 30 can be pushed distally toward the distal end of the surgical instrument 10 and, accordingly, toward the specimen "S" captured between grasper jaws 42 and 42'. According to various embodiments, the snare loop 34 associated with the specimen retrieval bag 30 can be maintained in a plane oriented substantially perpendicular to the line of longitudinal orientation of the grasper 40. In various embodiments, referring to FIG. 8, the specimen retrieval bag 30 can be further extended distally over the grasper jaws 42 and 42' of the grasper 40, beyond the distal end of the surgical instrument 10, and beyond the distal end of the specimen S to capture the specimen within the specimen retrieval bag 30. In various embodiments, referring to FIG. 7, second end 33 can be moved distally by snare 32 until specimen S is entirely covered by retrieval bag 30 as illustrated in FIG. 8. As described above, first end 31 of retrieval bag 30 can be affixed to grasper 40 such that, when second end 33 is pushed distally from its undeployed position, or configuration, into its deployed position, or configuration, retrieval bag 30 can be turned-inside-out, or inverted. In various circumstances, surgical instrument 10 and specimen S can then be removed from the surgical cavity through trocar 12. In other circumstances, trocar 12 can be withdrawn from the surgical site and the tissue wall T such that instrument 10 and specimen S can be withdrawn from the surgical cavity through the incision, or defect, previously made by or for trocar 12.

Figure 9:
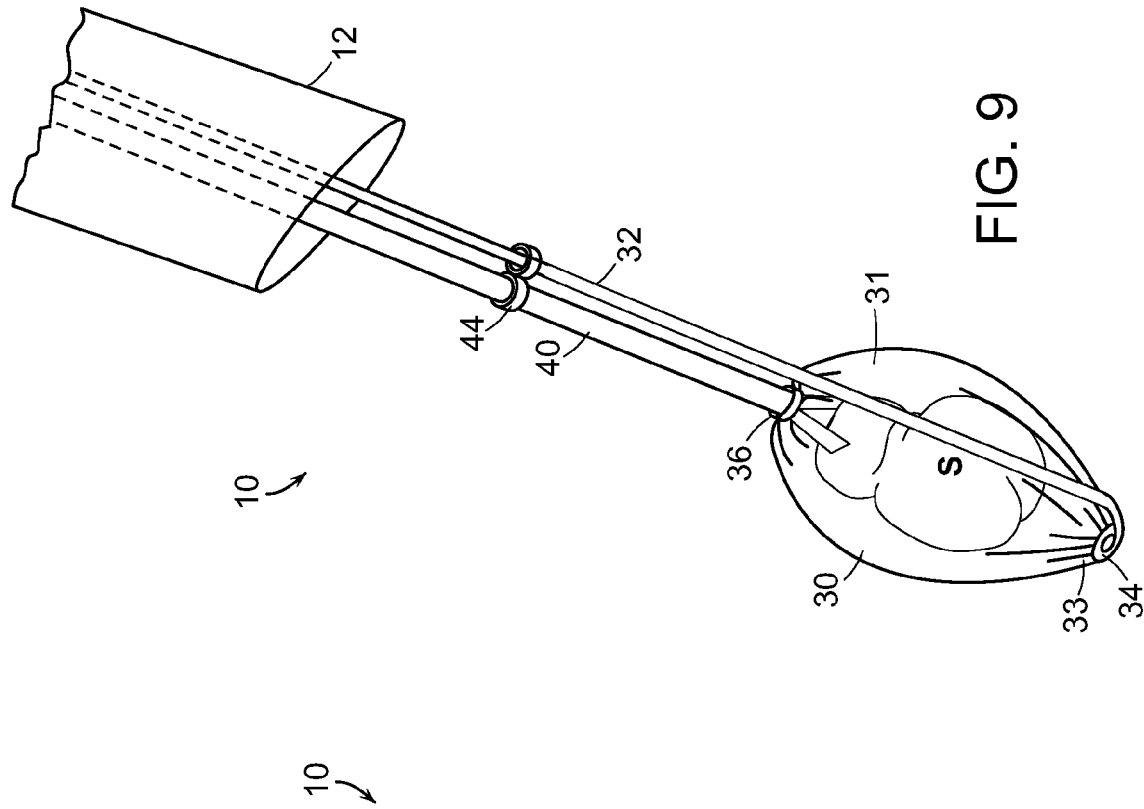
FIG. 9 is a diagram of the surgical instrument of FIG. 1 as the specimen retrieval bag is being collapsed, or at least partially closed, to capture the specimen.

In certain circumstances, it may be desirable to enclose, or at least substantially enclose, specimen S before it is removed from the surgical cavity. In such circumstances, the open, second end 33 of bag 30 can be closed before bag 30 and specimen S are removed from the surgical cavity. In certain embodiments, second end 33 can be closed by snare 32, for example. More particularly, snare loop 34 can be engaged with the perimeter of bag 30, or at least a portion of the perimeter of bag 30, such that, when the diameter, and/or circumference, of snare loop 34 is decreased, the perimeter of bag 30 can be drawn together, as illustrated in FIG. 9, thereby at least partially closing second end 33. In certain embodiments, second end 33 can be cinched such that it is completely closed. In embodiments where second end 33 is completely closed, bag 30 can comprise a fluid-tight arrangement where little, if any, fluids can leak out of the bag 30. In certain embodiments, bag 30 can be comprised of polyurethane and/or any other suitable material which can prevent, or at least limit, fluid from escaping from bag 30. In some embodiments, snare 32 can include a knotting or cinching element which can be configured to decrease the length of snare loop 34 when a pulling force is applied to snare 32, for example. Stated another way, a length of snare loop 34 can be pulled through the knotting or cinching element in order to reduce the diameter of the snare loop 34 and collapse the specimen retrieval bag 30 around the specimen S. Correspondingly, in various embodiments, the diameter and/or circumference of snare loop 34 can be increased by pushing a length of snare loop 34 through the cinching or knotting element such that the bag 30 can be selectively opened and/or closed.

As outlined above, a portion of retrieval bag 30 can be affixed to grasper 40, for example. In various alternative embodiments, a specimen retrieval bag may not be affixed to a grasper. In at least one embodiment, although not illustrated, the entire specimen retrieval bag can be slidable relative to the grasper such that the bag can be slid between a proximal position and a distal position. In certain circumstances, the grasper can be utilized to capture and control a specimen and the retrieval bag can be slid along the grasper until it at least partially covers the specimen. Accordingly, a surgical instrument can advantageously guide the retrieval bag as it is moved along the grasper such that the bag can be delivered directly to the specimen. Stated another way, the grasper, and/or any other suitable portion of a surgical instrument, can define a path for the specimen retrieval bag. As a result, such surgical instruments can provide an accurate and repeatable means by which to deliver a specimen retrieval bag and/or other suitable cover to a surgical site. In various embodiments, the proximal end of the bag can be at least partially closed before it is slid into place. In certain embodiments, the proximal end and/or the distal end of the bag can be at least partially closed after the bag has been suitably positioned relative to the specimen. In at least one embodiment, a surgical instrument can include a first actuator for positioning and/or closing a first end of a retrieval bag and a second actuator for positioning and/or closing a second end of the retrieval bag, wherein the first and second actuators can be selectively actuated in order to collapse, cover, and/or otherwise envelop the targeted specimen. In certain embodiments, at least a portion of a specimen retrieval bag can be detachably affixed to a surgical instrument such that the bag can be slid relative to a grasper, for example, after the bag has been detached from therefrom. In at least one embodiment, the retrieval bag can include at least one perforation, for example, which can be configured to allow the bag to release from the surgical instrument.

Figure 11:
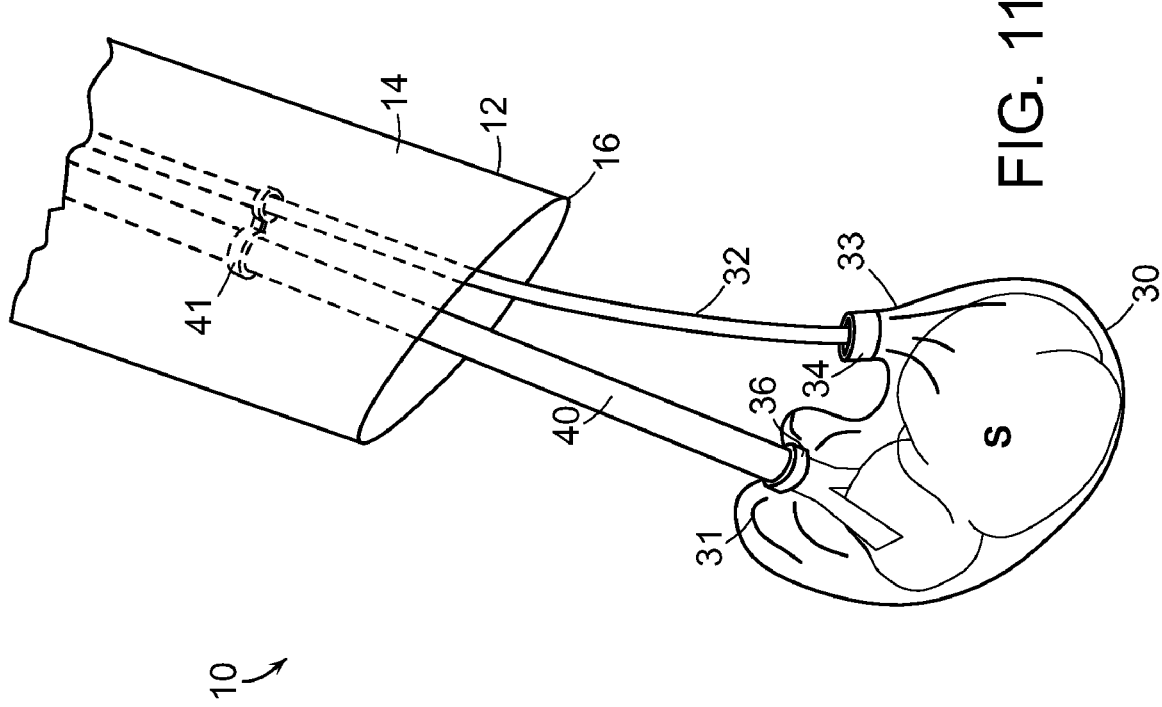
FIG. 11 is a diagram of the surgical instrument of FIG. 1 illustrating the specimen retrieval bag in a rotated position in accordance with at least one non-limiting embodiment of the present invention.
Figure 10:
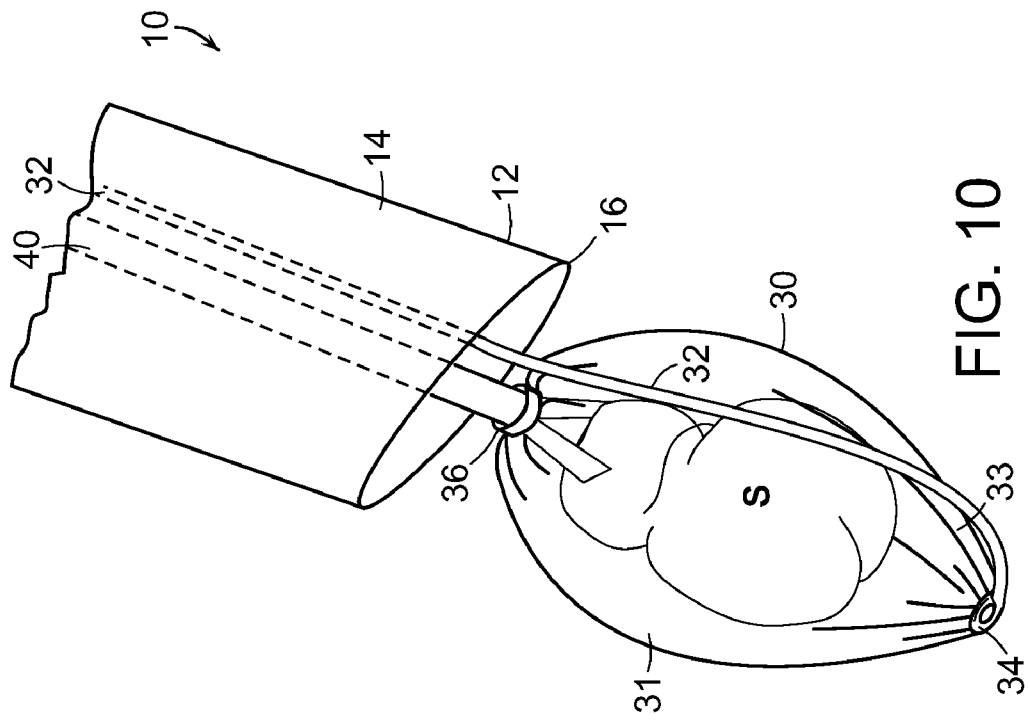
FIG. 10 is a diagram of the surgical instrument of FIG. 1 as the specimen retrieval bag is being retracted proximally into the trocar.

In various embodiments, as outlined above, the surgical instrument 10, including the grasper 40 and specimen retrieval bag 30, for example, can be retracted proximally into the trocar lumen 14 of the trocar 12, for example, in order to retrieve the specimen S from the surgical cavity. In certain embodiments, referring to FIG. 11, the bag actuator, or snare 32, can be utilized to rotate the specimen retrieval bag 30 within the surgical site. According to at least one such embodiment, snare 32 can be utilized to pull on second end 33 and move it proximally toward first end 31 thereby rotating retrieval bag 30. In certain embodiments, both ends 31 and 33 can be pulled into trocar 12 at the same time, or at least nearly the same time, in order to reduce the loss of tissue or fluid from the retrieval bag 30 during the retrieval procedure. In certain embodiments, although not depicted, the grasper 40 can be rotated, and/or otherwise suitably moved, relative to the other portions of the surgical instrument 10 in order to compress the specimen and/or reduce the volume of the specimen retrieval bag 30 and facilitate the removal of the captured specimen S through trocar 12. In certain embodiments, retrieval bag 30 can be detached from grasper 40 after the specimen has been at least partially captured within bag 30, for example, such that trocar 12 and/or the rest of surgical instrument 10 can be removed from the surgical site. In at least one such embodiment, the retrieval bag 30 can remain behind in the surgical site until snare 32, and/or any other suitable pull string, for example, is used to pull the retrieval bag 30 out of the surgical site.

Figure 13:
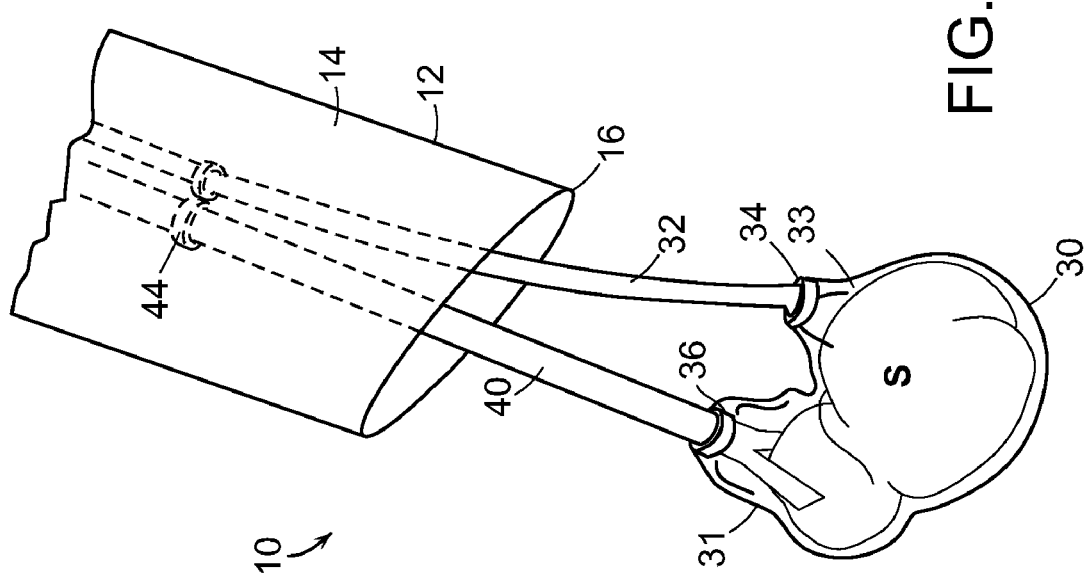
FIG. 13 is a diagram of the surgical instrument of FIG. 1 subsequent to the vacuum extraction of fluid from the rotated specimen retrieval bag in accordance with one non-limiting embodiment of the present invention.
Figure 12:
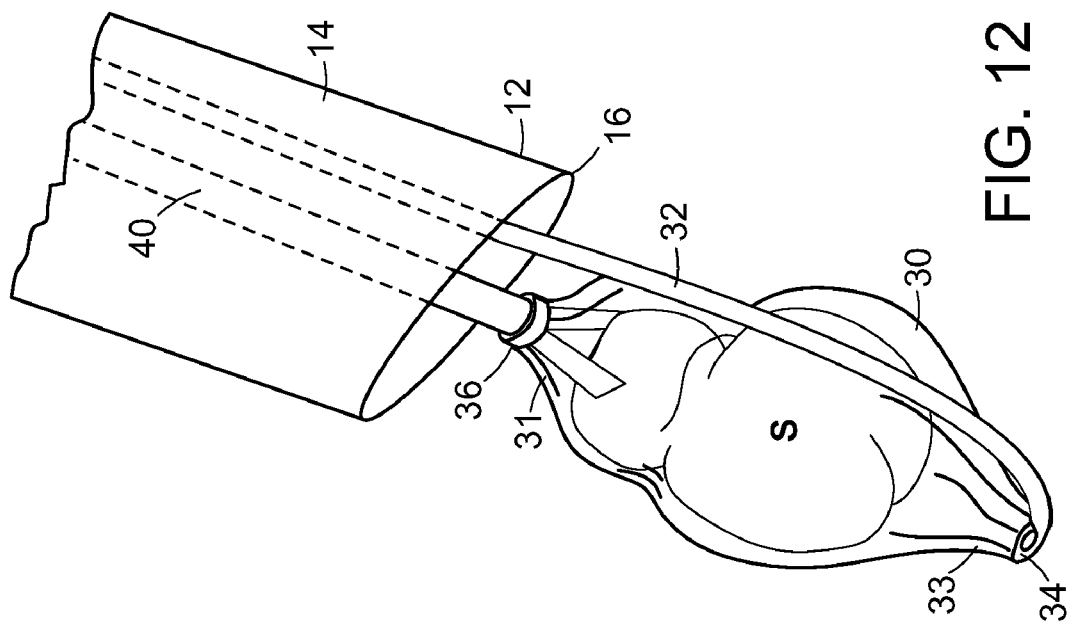
FIG. 12 is a diagram of the surgical instrument of FIG. 1 subsequent to the vacuum extraction of fluid from the specimen retrieval bag of FIG. 10 in accordance with one non-limiting embodiment of the present invention.

In various embodiments, referring to FIG. 12, a vacuum, or any suitable source of negative pressure (not shown), can be placed in fluid communication with retrieval bag 30 in order to draw air and/or other fluids out of retrieval bag 30. Removing air or other fluids from the specimen retrieval bag 30 can reduce the overall volume and/or size of the specimen retrieval bag 30 and facilitate the removal of the captured specimen "S" through the trocar lumen 14, for example. In certain embodiments, the vacuum can be placed in communication with bag 30 via at least one port, or aperture, in grasper 40, for example. In certain embodiments, the port or aperture can comprise the grasper lumen described above, for example. In use, the vacuum can be communicated to the retrieval bag 30 prior to rotating bag 30 as illustrated in FIG. 12 and/or after bag 30 has been rotated as illustrated in FIG. 13. In certain embodiments, a surgical instrument can further include a conduit which can be extended along and/or through grasper 40, for example, to supply bag 30 with the vacuum.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument can be obtained and if necessary cleaned. The instrument can then be sterilized. In one sterilization technique, the instrument can be placed in a closed and sealed container, such as a plastic or TYVEK bag. The container and instrument can then be placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A surgical instrument for use in removing a specimen from within the body of a patient, the surgical instrument comprising:
    a grasper comprising:
        a shaft;
        a distal end;
        a first jaw;

a second jaw, wherein said grasper is configured to capture a specimen between said first jaw and said second jaw;

a specimen retrieval bag movable between an undeployed position and a deployed position, wherein said specimen retrieval bag comprises a first opening and a second opening, wherein said grasper extends through said first opening and said second opening, and wherein said specimen retrieval bag comprises a covering surface and an outer surface, an attachment member, wherein at least a portion of said specimen retrieval bag surrounding said first opening is fixedly mounted to said shaft of said grasper by said attachment member at a bag attachment location, wherein said first jaw and said second jaw are closer to said distal end than said bag attachment location, wherein said second opening is movable relative to said first opening, wherein said second opening is larger than said first opening when said specimen retrieval bag is in said deployed position, and wherein said specimen retrieval bag is configured to at least partially surround the captured specimen when said specimen retrieval bag is in said deployed position; and an actuator operably engaged with said specimen retrieval bag at an actuator attachment location, wherein said actuator extends along said shaft of said grasper, wherein said specimen retrieval bag is inverted when said specimen retrieval bag is moved between said undeployed position and said deployed position, wherein said specimen retrieval bag is turned-inside-out when it is inverted, wherein said outer surface of said specimen retrieval bag is positioned adjacent to said shaft when said specimen retrieval bag is in said undeployed position, wherein said covering surface faces away from said shaft when said specimen retrieval bag is in said undeployed position, wherein said covering surface of said specimen retrieval bag is positioned adjacent to said shaft when said specimen retrieval bag is in said deployed position, wherein said outer surface faces away from said shaft when said specimen retrieval bag is in said deployed position, wherein said bag attachment location is closer to said distal end than said actuator attachment location when said specimen retrieval bag is in said undeployed position, and wherein said actuator attachment location is closer to said distal end than said bag attachment location when said specimen retrieval bag is in said deployed position.

2. The surgical instrument of claim 1, wherein said actuator comprises a snare loop configured to at least partially close said specimen retrieval bag.

3. The surgical instrument of claim 1, wherein said specimen retrieval bag defines a perimeter, and wherein said actuator comprises a snare engaged with at least a portion of said perimeter.

4. The surgical instrument of claim 1, further comprising an outer sheath, wherein said outer sheath is configured to at least partially surround said specimen retrieval bag when said specimen retrieval bag is in said undeployed position.

5. The surgical instrument of claim 4, wherein said outer sheath is slidable between a distal position in which said outer sheath at least partially surrounds said specimen retrieval bag and a proximal position in which said specimen retrieval bag can be moved between said undeployed position and said deployed position.

6. The surgical instrument of claim 1, further comprising a trocar including a trocar lumen, wherein said grasper and said specimen retrieval bag are slidably received within said trocar lumen.

7. The surgical instrument of claim 1, wherein said grasper further includes a grasper lumen, and wherein said grasper lumen is configured to place said specimen retrieval bag in fluid communication with a vacuum source.

8. The surgical instrument of claim 1, wherein said grasper is at least partially positioned within said specimen retrieval bag when said specimen retrieval bag is in said undeployed position.

9. The surgical instrument of claim 1, wherein said grasper is at least partially positioned within said specimen retrieval bag when said specimen retrieval bag is in said deployed position.

10. The surgical instrument of claim 1, wherein said shaft comprises:
a shaft outer surface; and
a distal guide extending from said shaft outer surface, wherein said actuator extends through said distal guide.

11. A surgical instrument for use in removing a specimen from within the body of a patient, the surgical instrument comprising:

a grasper comprising a shaft and at least one movable jaw, wherein said at least one movable jaw is configured to capture a specimen; and a specimen retrieval bag movable between an undeployed position and a deployed position, wherein said specimen retrieval bag comprises a first opening and a second opening, wherein said grasper extends through said first opening and said second opening, wherein said specimen retrieval bag comprises a covering surface and an outer surface, and wherein said specimen retrieval bag is configured to at least partially surround the captured specimen when said specimen retrieval bag is in said deployed position; and an attachment member, wherein said specimen retrieval bag includes a first end and a second end, wherein said first end is affixed to said grasper by said attachment member at a bag attachment location, wherein said second end is positioned proximal with respect to said first end when said specimen retrieval bag is in said undeployed position, and wherein said second end is positioned distal with respect to said first end when said specimen retrieval bag is in said deployed position; and an actuator operably engaged with said specimen retrieval bag at an actuator attachment location, wherein said actuator extends along said grasper, wherein said specimen retrieval bag is inverted when said specimen retrieval bag is moved between said undeployed position and said deployed position, wherein said specimen retrieval bag is turned-inside-out when it is inverted, wherein said outer surface of said specimen retrieval bag is positioned adjacent to said shaft when said specimen retrieval bag is in said undeployed position, wherein said covering surface faces away from said shaft when said specimen retrieval bag is in said undeployed position, wherein said covering surface of said specimen retrieval bag is positioned adjacent to said shaft when said specimen retrieval bag is in said deployed position, wherein said outer surface faces away from said shaft when said specimen retrieval bag is in said deployed position, wherein said bag attachment location is closer to said at least one movable jaw than said actuator attachment location when said specimen retrieval bag is in said undeployed position, and wherein said actuator attachment location is closer to said at least one movable jaw than said bag attachment location when said specimen retrieval bag is in said deployed position.

12. The surgical instrument of claim 11, wherein said grasper comprises:
   a grasper outer surface; and
   a distal guide extending from said grasper outer surface, wherein said actuator extends through said distal guide.

13. A surgical kit for use in removing a specimen within the body of a patient, the kit comprising:
   a grasper comprising a shaft, wherein said grasper is configured to capture a specimen;
   a specimen retrieval bag slidable relative to said grasper, wherein said specimen retrieval bag comprises a covering surface and an outer surface, wherein said specimen retrieval bag is movable between an undeployed position and a deployed position, wherein said specimen retrieval bag comprises a first opening and a second opening, wherein said grasper is configured to extend through said first opening and said second opening, wherein at least a portion of said specimen retrieval bag surrounding said first opening is affixed to said shaft of said grasper at a bag attachment location, wherein said second opening is movable relative to said first opening, and wherein said specimen retrieval bag is configured to at least partially surround the captured specimen when said specimen retrieval bag is in said deployed position; and
   an actuator operably engaged with said specimen retrieval bag at an actuator attachment portion, wherein said actuator extends along said shaft of said grasper, and wherein said actuator is movable between:
      a first position in which said actuator attachment portion is positioned proximally with respect to said bag attachment location and said specimen retrieval bag is in said undeployed position; and
      a second position in which said actuator attachment portion is positioned distally with respect to said bag attachment location and said specimen retrieval bag is in said deployed position, wherein said specimen retrieval bag is inverted when said specimen retrieval bag is moved between said undeployed position and said deployed position, wherein said specimen retrieval bag is turned-inside-out when it is inverted, wherein said outer surface of said specimen retrieval bag is positioned adjacent to said shaft when said specimen retrieval bag is in said undeployed position, wherein said covering surface faces away from said shaft when said specimen retrieval bag is in said undeployed position, wherein said covering surface of said specimen retrieval bag is positioned adjacent to said shaft when said specimen retrieval bag is in said deployed position, and wherein said outer surface faces away from said shaft when said specimen retrieval bag is in said deployed position.

14. The surgical kit of claim 13, wherein said grasper further includes a grasper lumen, and wherein said grasper lumen is configured to place said specimen retrieval bag in fluid communication with a vacuum source.

15. The surgical kit of claim 13, wherein said grasper is at least partially positioned within said specimen retrieval bag when said specimen retrieval bag is in said undeployed position.

16. The surgical kit of claim 13, wherein said grasper is at least partially positioned within said specimen retrieval bag when said specimen retrieval bag is in said deployed position.

17. The surgical kit of claim 13, wherein said shaft comprises:
   a shaft outer surface; and
   a distal guide extending from said shaft outer surface, wherein said actuator extends through said distal guide.

* * * * *